US00PP17946P3

(12) United States Plant Patent
Abrahamson et al.

(10) Patent No.: US PP17,946 P3
(45) Date of Patent: Aug. 28, 2007

(54) FAST-GROWING WILLOW SHRUB NAMED 'TULLY CHAMPION'

(50) Latin Name: ***Salix viminalis*×*Salix miyabeana***
Varietal Denomination: Tully Champion

(75) Inventors: Lawrence P. Abrahamson, Marcellus, NY (US); Richard F. Kopp, Marietta, NY (US); Lawrence B. Smart, Geneva, NY (US); Timothy A. Volk, Syracuse, NY (US)

(73) Assignee: The Research Foundation of State University of New York, Albany, NY (US)

( * ) Notice: Subject to any disclaimer, the term of this patent is extended or adjusted under 35 U.S.C. 154(b) by 102 days.

(21) Appl. No.: 11/244,635

(22) Filed: Oct. 6, 2005

(65) Prior Publication Data

US 2007/0083958 P1 Apr. 12, 2007

(51) Int. Cl.
*A01H 5/00* (2006.01)

(52) U.S. Cl. ..... Plt./216

(58) Field of Classification Search ..... Plt./216
See application file for complete search history.

*Primary Examiner*—Kent Bell
(74) *Attorney, Agent, or Firm*—Wall Marjama & Bilinski LLP

(57) ABSTRACT

A distinct female cultivar of *Salix viminalis*×*S. miyabeana* named 'Tully Champion', characterized by rapid stem growth producing greater than 25% more woody biomass than two current production clones (*Salix dasyclados* 'SV1' and *Salix miyabeana* 'SX64'), more than 2.5-fold greater biomass than one of its parents (*Salix miyabeana* 'SX67'), and nearly 3-fold more biomass than another production clone (*Salix sacchalinensis,* 'SX61') when grown in the same field for the same length of time (two growing seasons after coppice) in Tully, N.Y. 'Tully Champion' can be planted from dormant stem cuttings, produces multiple stems after coppice, and the stem biomass can be harvested when the plant is dormant. In the spring following harvest, the plant will re-sprout very vigorously, producing new stems that can be harvested repeatedly after two to four years of growth. 'Tully Champion' displays a low incidence of rust disease and is not damaged by potato leafhoppers.

10 Drawing Sheets

STATEMENT AS TO RIGHTS TO INVENTIONS MADE UNDER FEDERALLY-SPONSORED RESEARCH AND DEVELOPMENT

The invention described herein was reduced to practice during the funding period of Contract 4000003235 (SUNY Research Foundation Award 011275) awarded by Oak Ridge National Laboratory, managed by UT-Batelle for the United States Department of Energy under contract DE-AC05-00OR22725, and of agreement number 6267 (SUNY Research Foundation Award 011536) awarded by the New York State Energy Research and Development Authority.

CROSS-REFERENCE TO RELATED APPLICATIONS

This application is related to the following plant patent application, all of which are subject to assignment to the Research Foundation of the State University of New York, and each of which is being filed on even date herewith: "Fast-Growing Shrub Willow" Named 'Fish Creek', application Ser. No. 11/244,988; "Fast-Growing Shrub Willow" Named 'Canastota', application Ser. No. 11/244,986; "Fast-Growing Shrub Willow" Named 'Millbrook', application Ser. No. 11/244,636; "Fast-Growing Shrub Willow" Named 'Oneida', application Ser. No. 11/244,975; "Fast-Growing Shrub Willow" Named 'Otisco', application Ser. No. 11/244,987; and "Fast-Growing Shrub Willow" Named 'Owasco', application Ser. No. 11/244,842. The variety of fast-growing shrub willow named 'Tully Champion' was produced in the same willow breeding program as were other varieties, including: 'Fish Creek', 'Canastota', 'Millbrook', 'Oneida', 'Otisco', and 'Owasco'.

BACKGROUND OF THE INVENTION

1. Field of the Invention

The invention is a new and distinct cultivar known by the varietal name 'Tully Champion' resulting from the novel hybridization of *Salix viminalis* with *Salix miyabeana.* The new variety was produced through controlled willow breeding conducted by the inventors in Syracuse, N.Y. The objective of the breeding program is to produce new willow cultivars that generate high biomass yields on a variety of sites, are resistant to diseases and pests, and possess agronomic traits suitable for mechanical planting, harvesting, and post-harvest processing. Shrub willow is being developed as an agricultural crop plant that will be grown and harvested as a sustainable, renewable source of energy. Once a field planting of shrub willows is established, the woody stems can be harvested every three years, and new shoots will re-sprout the following season. Repeated harvesting every two to four years can be sustained for at least 15 years.

2. Description of Relevant Prior Art Including Information Disclosed under 37 CFR 1.97-1.99

This new variety of *Salix viminalis*×*Salix miyabeana* was the seedling progeny of the controlled pollination of the female clone *Salix viminalis* 'SV2' by the male clone *Salix miyabeana* 'SX67' performed in February 1999 in Syracuse, N.Y. The female parent (*Salix viminalis* 'SV2') has leaves that are narrowly lanceolate and with acute apex. They are pubescent underneath with raised veins. Margins are entire and leaves average 8.0–12.0 cm in length and 1.0–1.5 cm in width. Variety 'Tully Champion' leaves are more oblong to oblong-lanceolate, apex acuminate, margins irregularly glandular-serrulate or subentire, averaging 15.2–21.5 cm in length and 2.2–3.0 cm in width. The leaves are glabrous underneath. The plant has been propagated repeatedly by stem cuttings and has been found to retain its distinctive characteristics through successive propagations and field trials. More specifically, the plant has been asexually reproduced by collecting dormant stems during the winter months, cutting them into either 5 inch or 10 inch pieces (cuttings), then planting those cuttings in the field in the spring or in potting mix in the greenhouse, then transplanting the rooted cuttings to the field.

Both parents were originally transferred from the Toronto, Ontario, Canada, to Syracuse, N.Y., were vegetatively propagated from stem cuttings. The female parent (*S. viminalis* 'SV2') was transferred in 1990, while the male parent (*Salix miyabeana* 'SX67') was transferred in 1994. The growth of the parent plants was characterized in nursery plantings. The male clone *Salix miyabeana* 'SX67' displayed rapid stem growth and low incidence of rust disease, so was chosen to serve as a parent in a cross with *S. viminalis* 'SV2', which suffered from susceptibility to the potato leafhopper (*Empoasca fabae*). The seedlings produced by this cross (identification #99202) were first established in a greenhouse, and then were transplanted to a field in Syracuse, N.Y. This particular individual (identification #99202-011) was selected from the family due to its exceptional stem height growth.

The new cultivar has been grown in Syracuse, N.Y. and Tully, N.Y., which have a normal yearly average daily temperature of 47° F., normal daily maximum temperature in July of 82° F., normal daily minimum temperature in January of 14° F., and average precipitation of 40 inches. The new cultivar grows from a rooted cutting to a fully mature plant ready for harvest in approximately three years.

SUMMARY OF THE INVENTION

The *Salix viminalis*×*Salix miyabeana* cultivar 'Tully Champion' has not been observed under all possible environmental conditions. The phenotype may vary somewhat with variations in environments such as temperature, light intensity and length of illumination, without, however, any variation in genotype. The new and distinct cultivar presents the following traits that have been repeatedly observed and are determined to be the unique characteristics of 'Tully Champion'. These characteristics in combination distinguish 'Tully Champion' as a new and distinct cultivar:

1. Rapid growth rate, producing greater than 25% more woody biomass than two current production clones (*Salix dasyclados* 'SV1' and *Salix miyabeana* 'SX64'), more than 2.5-fold greater biomass than one of its parents (*Salix miyabeana* 'SX67'), and nearly 3-fold more biomass than another production clone (*Salix sacchalinensis,* 'SX61') when grown in the same field for the same length of time (two growing seasons after coppice) in Tully, N.Y.
2. Resistance to potato leafhopper, which causes severe stunting of growth, curling of the leaves, and overall decline in vigor (all characteristic of hopper burn) on the female parent, *S. viminalis* 'SV2'.
3. Low incidence of rust disease assessed in experimental trials in Syracuse, N.Y. in 2000.

BRIEF DESCRIPTION OF THE DRAWING

The accompanying color photographs show the features of the claimed cultivar in a manner as true as is reasonably possible. The illustrations include:

FIG. 1.2 illustrates one-year-old portion of stem collected while dormant;

FIG. 1.3 illustrates a vegetative bud in dormancy;

FIG. 1.4 illustrates a floral bud in dormancy;

FIG. 1.5 illustrates new shoot growth from a stem cutting rooted in soil:sand in a greenhouse;

FIG. 1.6 illustrates upper leaf surface;

FIG. 1.7 illustrates lower leaf surface;

FIG. 1.8 illustrates mature catkin;

FIG. 1.9 illustrates pistil and densely pubescent floral bract; and

FIG. 2.1 illustrates the Biomass Yield two years after coppice—Tully N.Y.

DETAILED DESCRIPTION OF THE NEW PLANT

Figure 1:
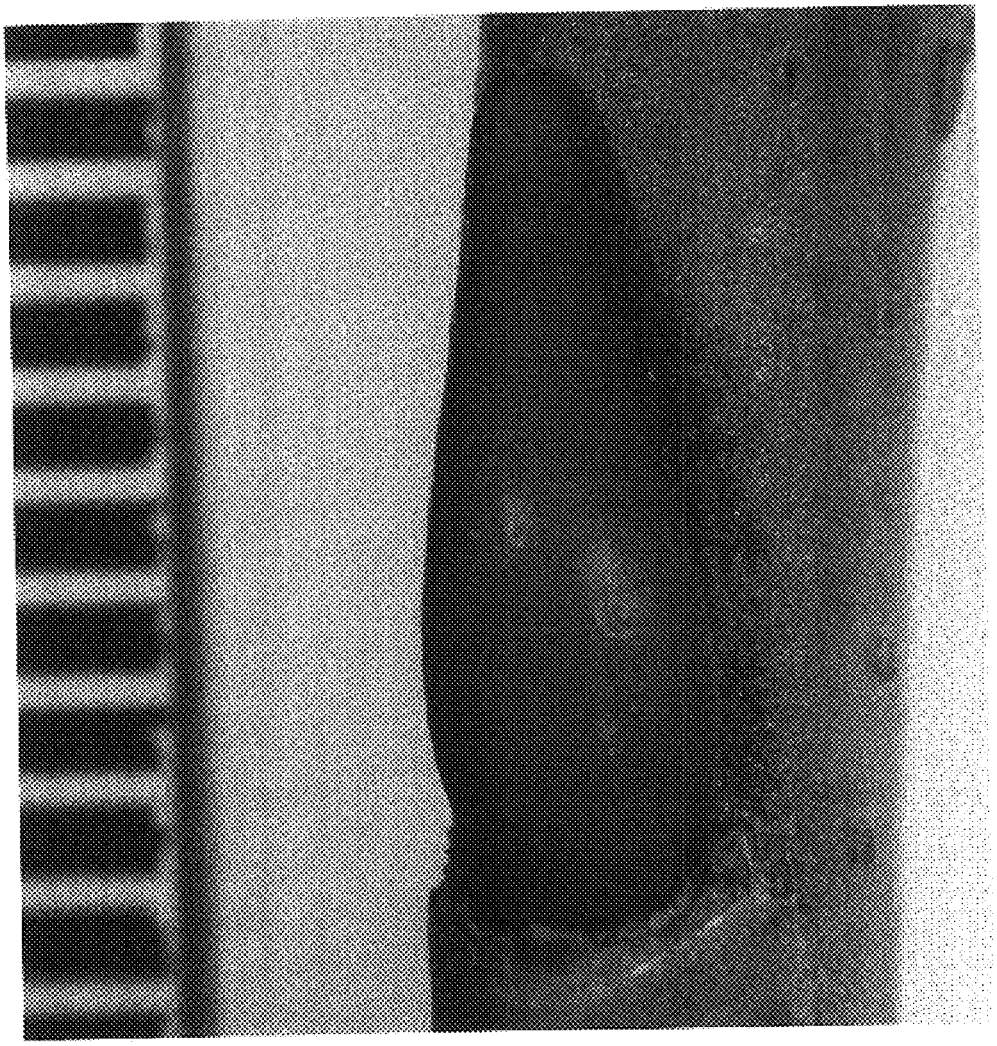
FIG. 1.1 illustrates two-year-old portion of stem collected while dormant.

The following detailed description sets forth characteristics of the new plant. The following observations and measurements describe plants grown by asexual reproduction in Syracuse, N.Y. or Tully, N.Y. under conditions as described hereinabove. Color references are made using The Royal Horticultural Society Colour Chart (hereinafter the R.H.S. Colour Chart) of The Royal Horticultural Society of London, England, except where general terms of ordinary dictionary significance are used.

BOTANICAL DESCRIPTION OF THE PLANT

The following detailed description of the 'Tully Champion' variety is based on observations from 10 inch cuttings grown in a greenhouse in Syracuse, N.Y. Cuttings were grown in 7 inch tubes in a (1:1) ProMix®/sand (v/v) substrate under natural light from December 2004 to March 2005. Plants were irrigated with automatic misting for 6 minutes every 2 hours five times each day.

Latin name: *Salix viminalis*×*S. miyabeana.*
Varietal denomination: 'Tully Champion'.
Parentage:
*Female or seed parent.*—*S. viminalis* 'SV2'.
*Male or pollen parent.*—*S. miyabeana* 'SX67'.
Propagation:
*Type.*—Stem cutting.
*Time to rooting.*—Approximately 10 days in water at 21° C.
Precocity: Precocious — Catkins mature several days before leaves break bud.
Plant description: The color of one-year-old stem cuttings observed when dormant are grey orange (RHS 168B), while two to three-year-old stems are yellow-green (RHS 152C), lustrous, and glaucous in some places. Vegetative buds are red (RHS 168B), ovoid, and acute in two to three-year-old stems, and elongated in one-year-old growth with pubescence behind the buds. Lenticels are reddish brown to tan, large, wart-like, and numerous. The leaves are simple and alternate with pinnate venation. Average pistils are 2 mm in length. Petioles are typically 4 mm in length, 1.7–2.1 mm in diameter, and greenyellow (#1D). Stipules are typically 3–4 mm in length, narrow, curved, serrulate, and green (#137B). Immature leaves have a few small hairs. Mature leaves are lanceolate, acuminate apex, acute base, typically 7.5–9.0 cm in length, 1.0–1.5 cm in width, sometimes undulate, and serrate margin, adaxial (upper) surface green (RHS 144B), pale green abaxial (lower) surface (RHS 145A), and light pale green stem (RHS 145B) at 7½ weeks of growth. The upper surfaces of the leaves is glabrous, glossy, and green (#135A) with distinct pinnate venation. The lower surface is glabrous and green (#137A). The average diameter of the trunk (two year old stem) at a height of 1 m is 1.5 cm. The bark color of the two-year old field grown stem is yel/grn (152C). The surface is slightly rough with shallow longitudinal lenticles. The average height of a mature plant after three years of growth is 5–6 m with a spread at the crown of 1.0–1.5 m in the typical planting space of 0.6 m×0.7 m.

Flowering description: Dormant floral buds are elongated, ovoid, acute, beak-like apex, typically 9 mm in length, slightly raised to form a very small acute angle with the stem, and red (N34A). Peduncle of catkin is short and bears 4 leafy bracts. Catkins are erect, typically 3.6 mm in length, narrowly cylindrical, and densely flowered. Flowers have a pubescent medium sized sessile ovary with a medium length style and 2 erect, slightly separated stigmas. Floral bract is densely pubescent with a dark acute apex and a pink base.

Field growth characteristics: Determined through surveys of plants growing in the field in Tully, N.Y. and in Syracuse, N.Y.

Disease resistance: Displays a low incidence of rust disease.

Temperature tolerance: Stems typically do not suffer frost damage at temperatures as low as 10° F. and may suffer only minor tip dieback at lower temperatures.

Seed production: 'Tully Champion' produces only female flowers, so viable seeds will only be produced after pollination by a compatible male variety. This has not yet been observed in field trials.

Biomass yield: Mean dry stem biomass yield produced through two growing seasons after coppice in each of eight four-plant plots ('Tully Champion', 14.02 oven dry tons $ha^{-1}$ $yr^{-1}$) measured in a yield trial growing in Tully, N.Y. in February 2005 was 2.5-fold greater than the mean stem biomass yield of one of its parents ('SX67', 5.52 oven dry tons $ha^{-1}$ $yr^{-1}$); was more than 25% greater than current production cultivars ('SV1', 11.04 oven dry tons $ha^{-1}$ $yr^{-1}$ and 'SX64', 10.35 oven dry tons $ha^{-1}$ $yr^{-1}$); and was nearly 3-fold greater than the mean stem biomass yield of another production cultivar ('SX61'; 4.83 oven dry tons $ha^{-1}$ $yr^{-1}$) growing in the same trial (FIG. 2.1).

What is claimed is:

1. A new and distinct variety of *Salix viminalis*×*S. miyabeana* plant, substantially as illustrated and described herein.

* * * * *

Fig. 1.1
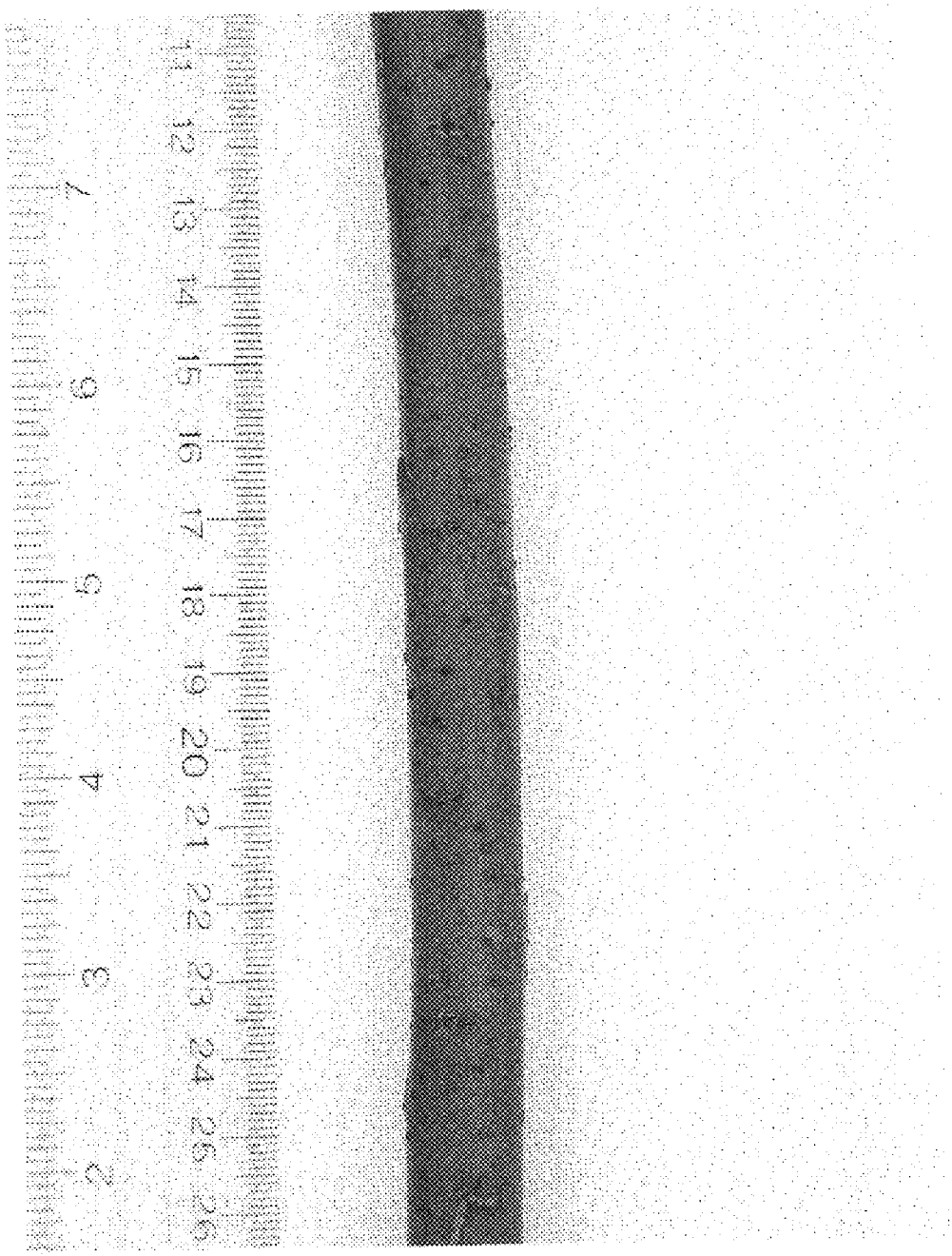

Fig. 1.2
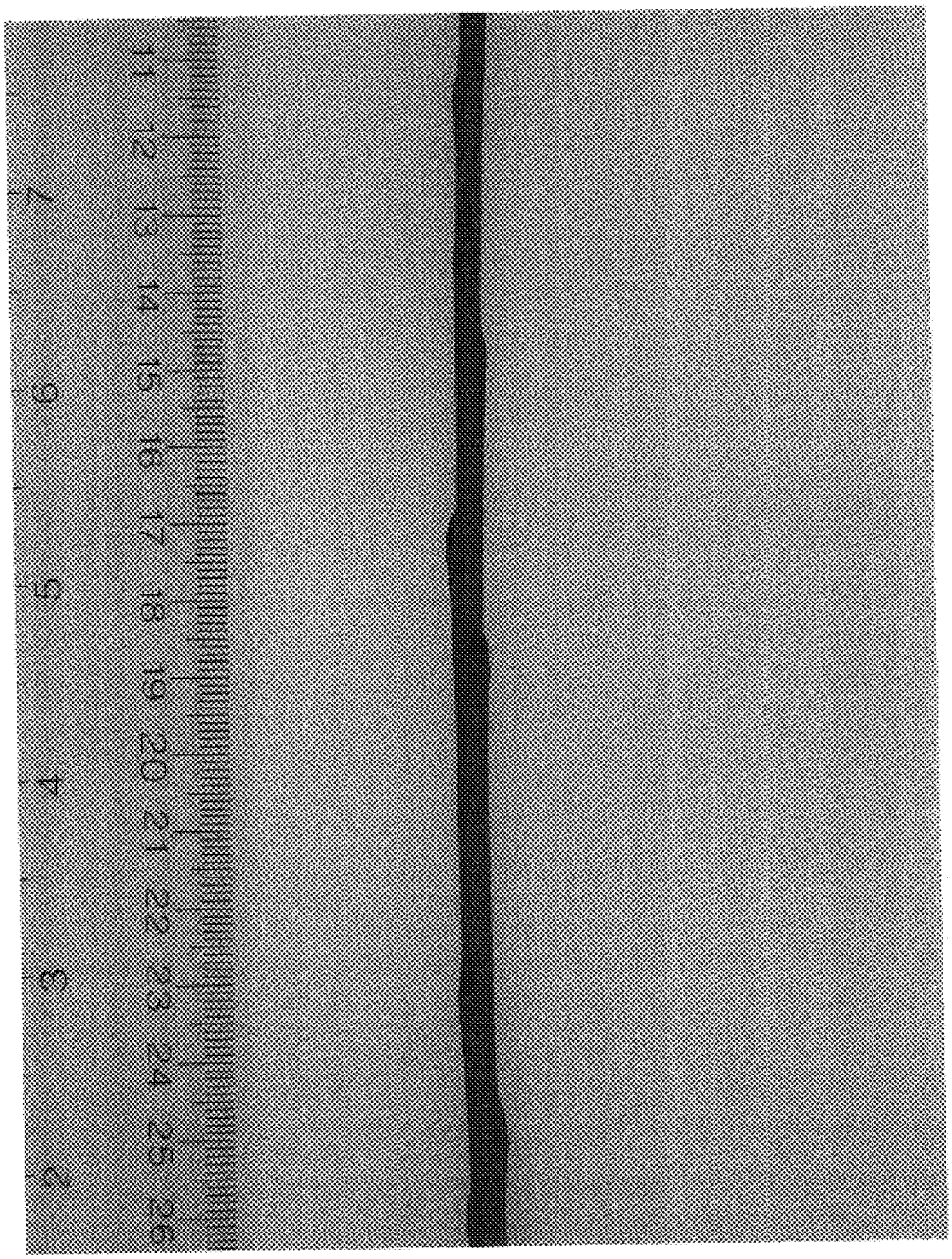

Fig. 1.3
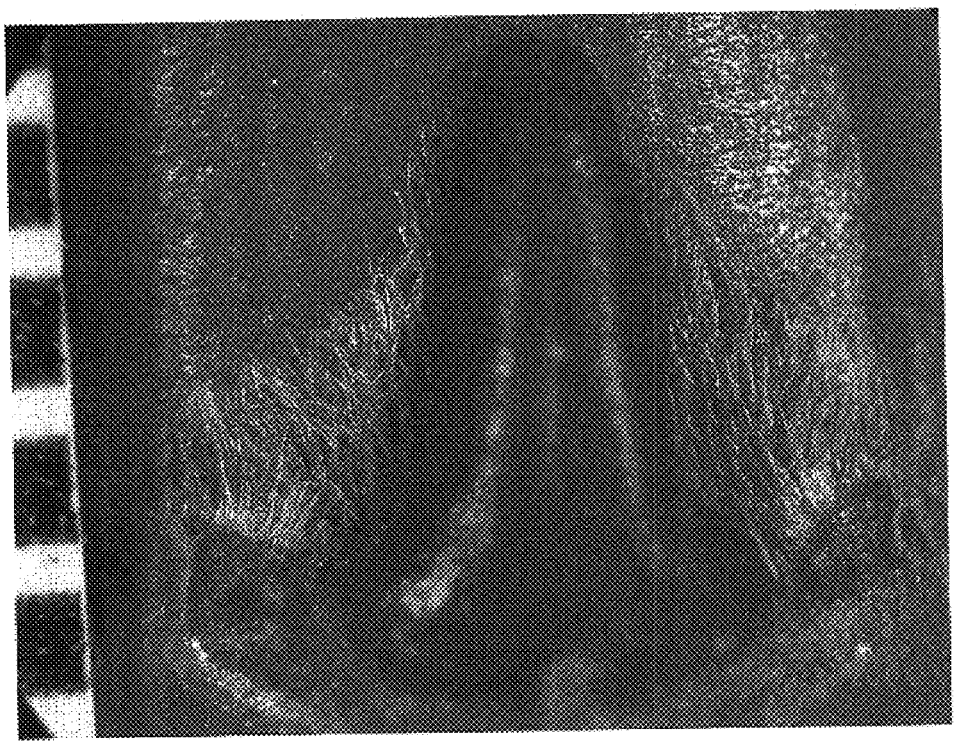

Fig. 1.5
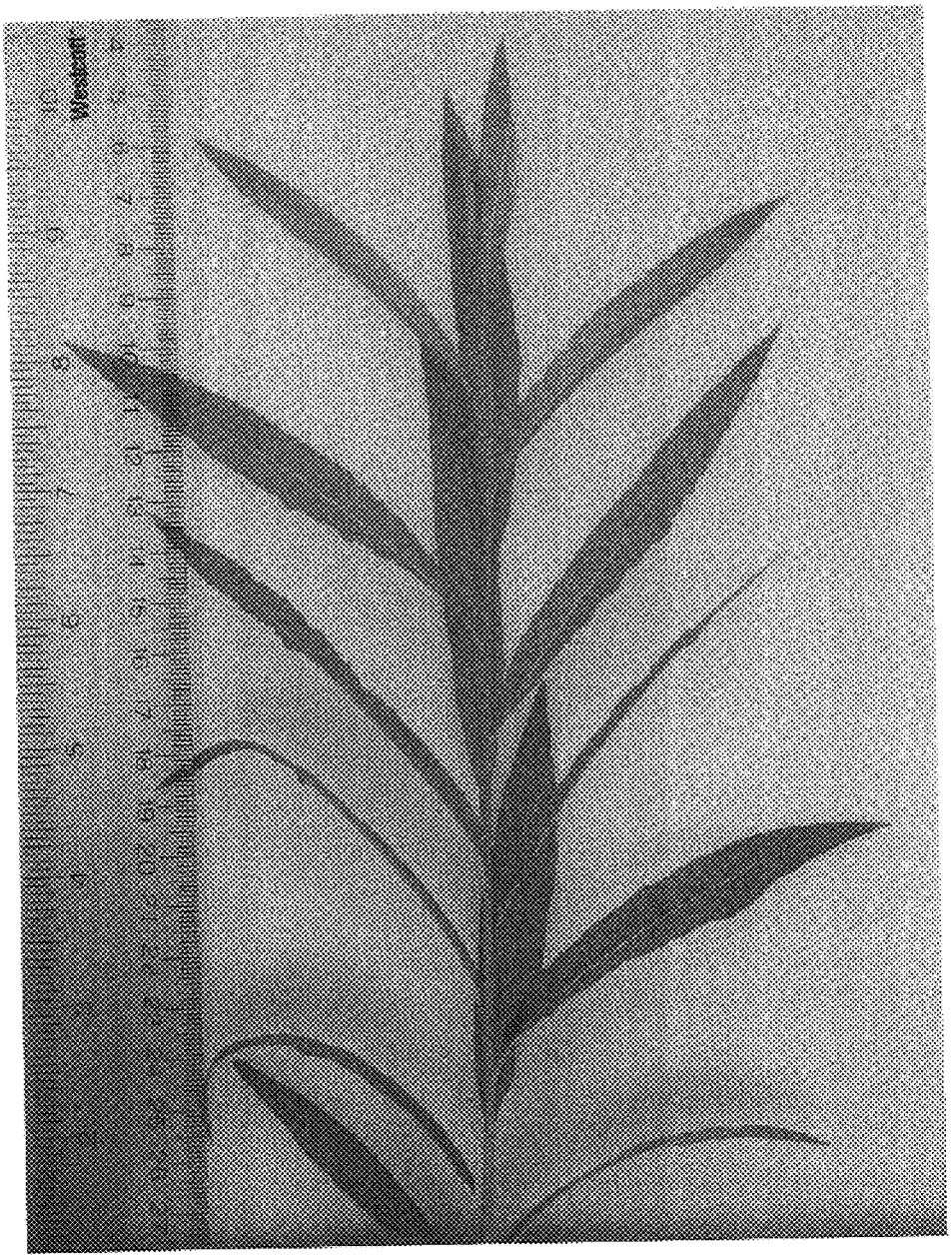

Fig. 1.6
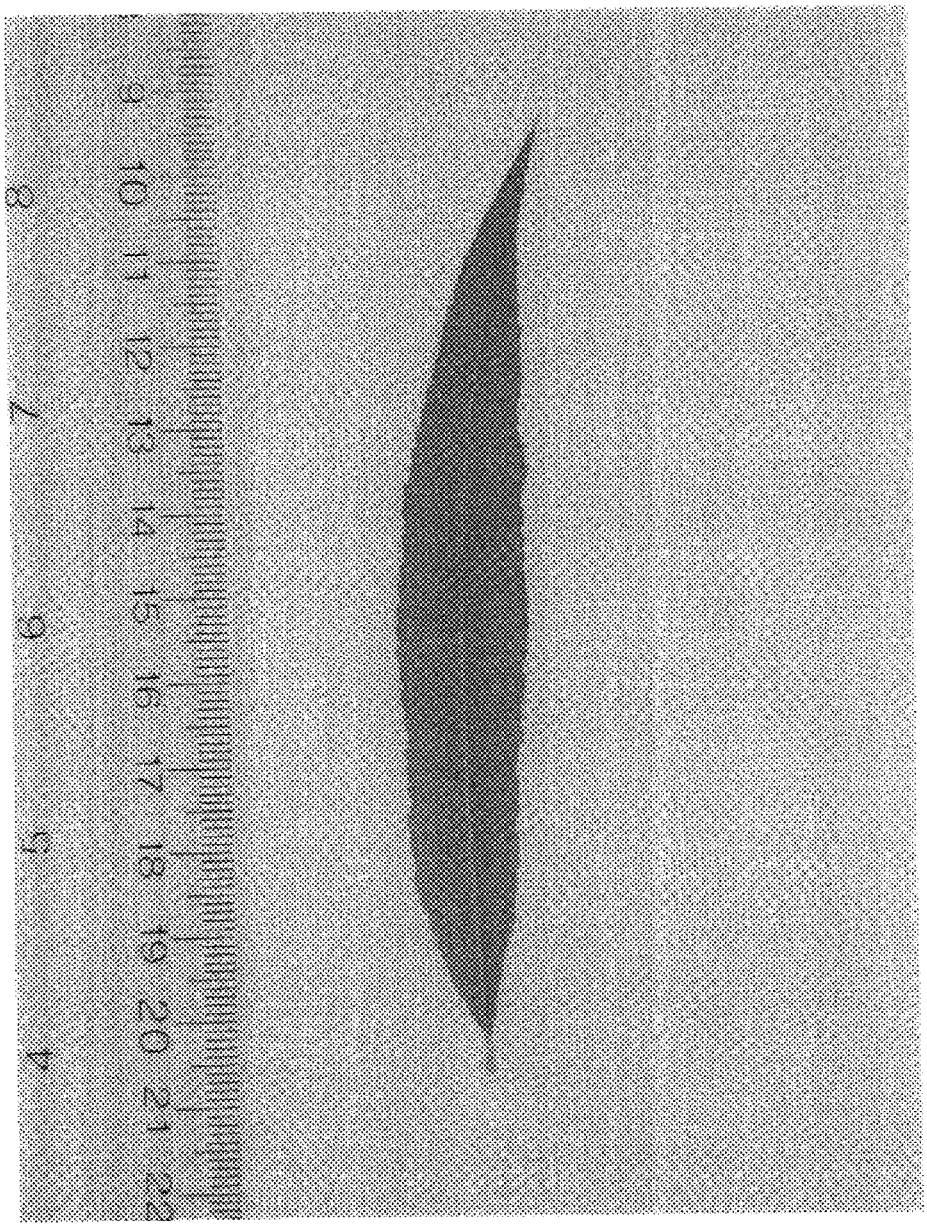

Fig. 1.7
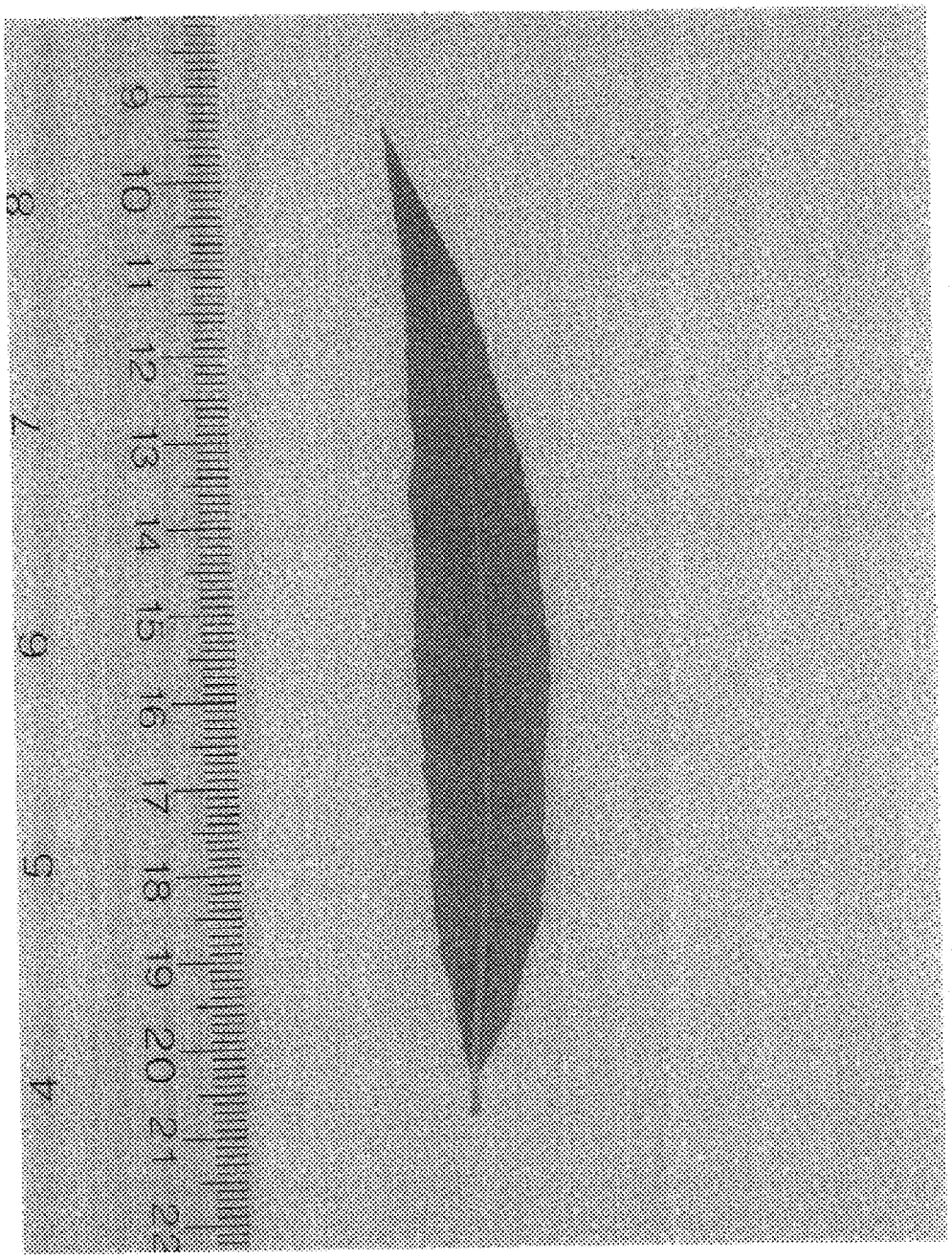

Fig. 1.8
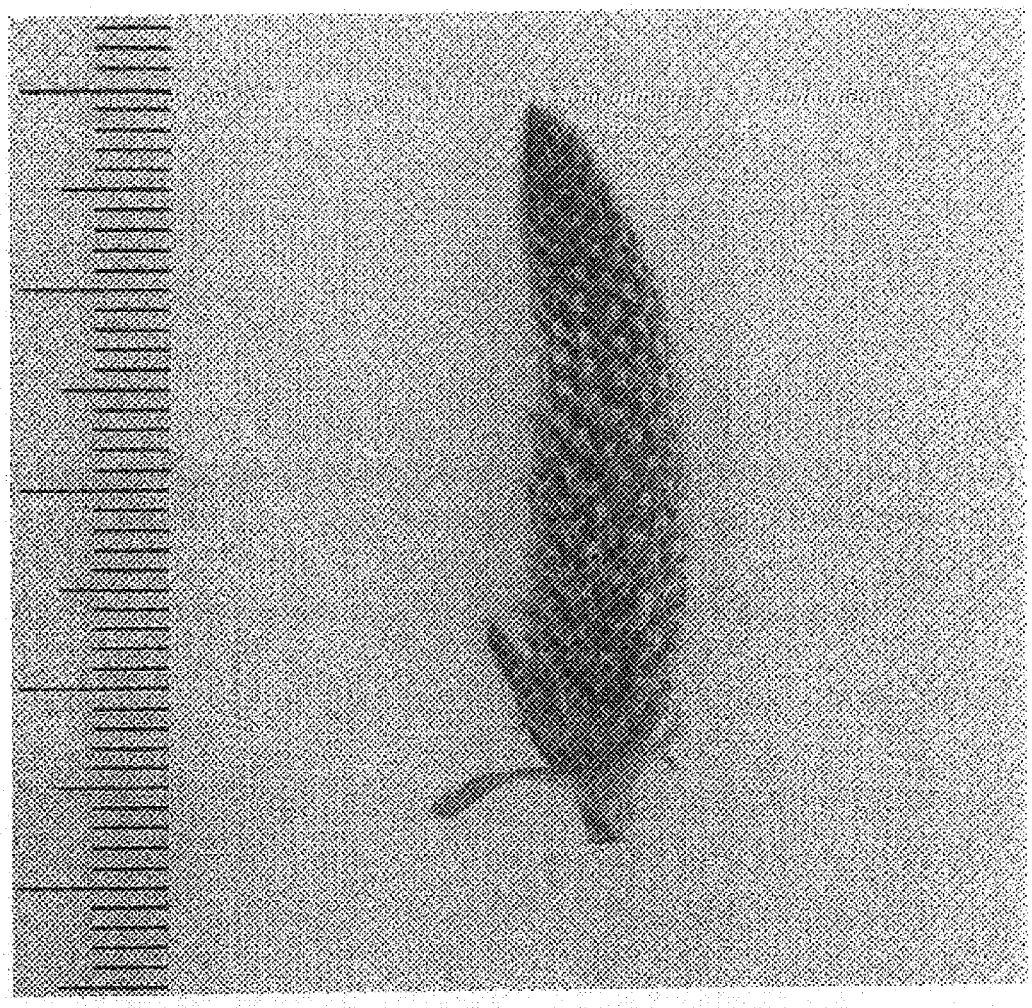

Fig. 1.9
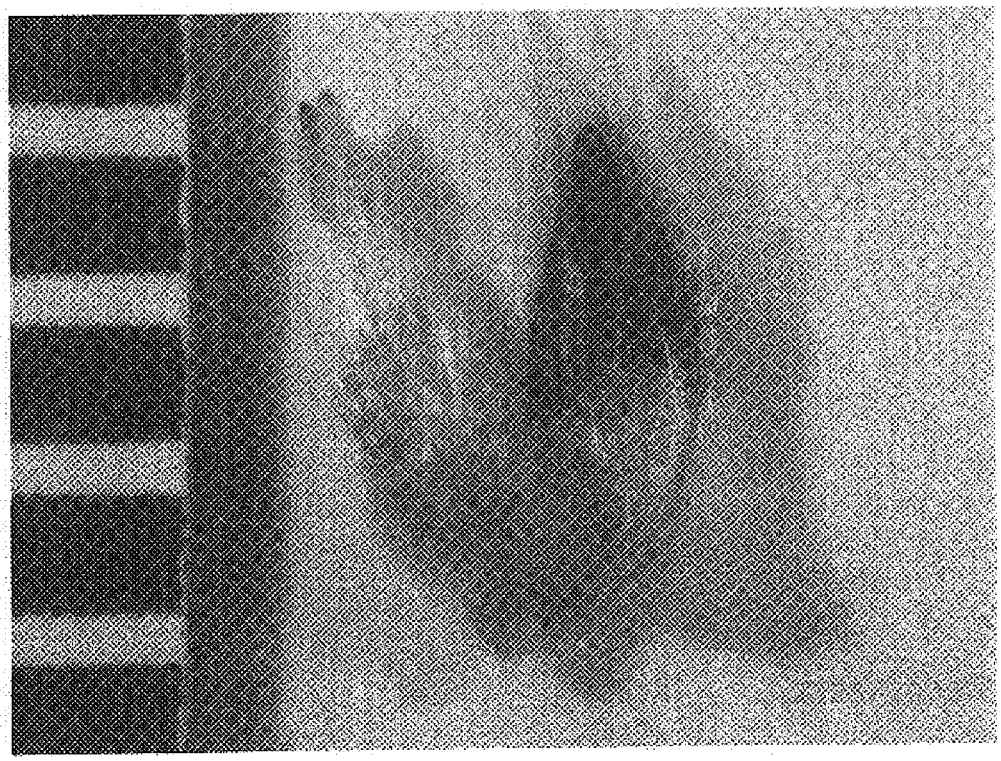

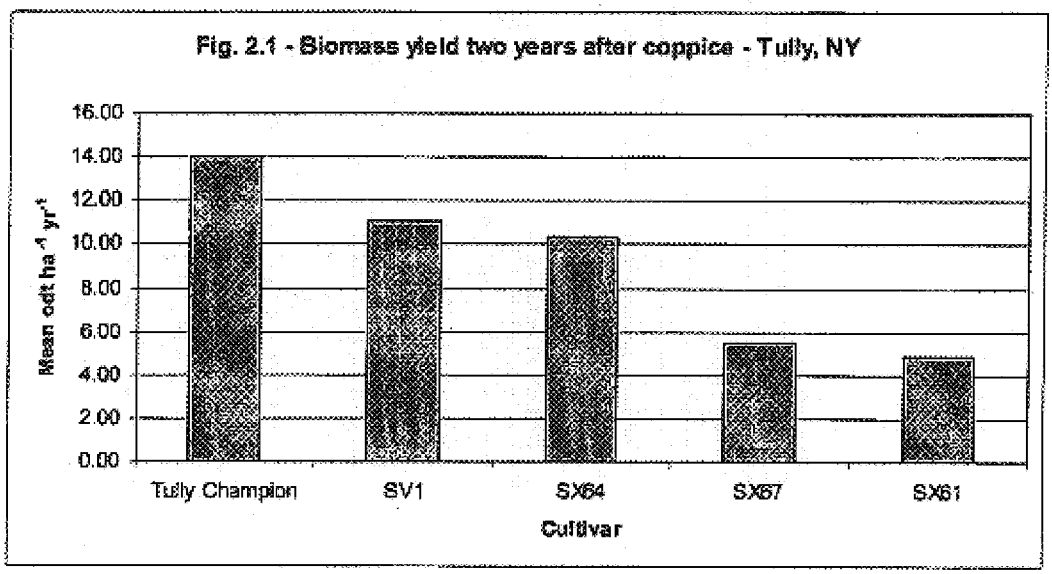
Fig. 2.1 - Biomass yield two years after coppice - Tully, NY
16.00
14.00
12.00
10.00
8.00
6.00
4.00
2.00
0.00
Mean odt ha-1 yr-1
Tully Champion
SV1
SX64
SX67
SX61
Cultivar